US00PP32960P2

(12) United States Plant Patent
Avent

(10) Patent No.: US PP32,960 P2
(45) Date of Patent: Apr. 6, 2021

(54) ***HOSTA* PLANT NAMED 'TIME TRAVELER'**

(50) Latin Name: ***Hosta* hybrid**
Varietal Denomination: Time Traveler

(71) Applicant: Tony Avent, Raleigh, NC (US)

(72) Inventor: Tony Avent, Raleigh, NC (US)

( * ) Notice: Subject to any disclaimer, the term of this patent is extended or adjusted under 35 U.S.C. 154(b) by 0 days.

(21) Appl. No.: 16/602,889

(22) Filed: Dec. 18, 2019

Related U.S. Application Data

(60) Provisional application No. 62/917,835, filed on Dec. 29, 2018.

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 5/02
See application file for complete search history.

(56) References Cited

PUBLICATIONS https://www.twincities.com/2018/03/03/blundering-gardener-as-spring-approaches-i-dream-of-hostas/; Mar. 3, 2018; 0 pages.*

* cited by examiner

*Primary Examiner* — Kent L Bell

(57) ABSTRACT

A new and unique cultivar of *Hosta* named *Hosta* 'Time Traveler' with each round, corrugated, chartreuse-yellowish, pointed leaf having a gray green center, white-edged *Hosta* leaf sown in the middle between the chartreuse-yellowish and the gray green.

1 Drawing Sheet

Botanical classification: *Hosta* hybrid.
Variety denomination: 'Time Traveler'.

BACKGROUND OF THE INVENTION

The present invention relates to a new and distinct cultivar of *Hosta* plant, known as *Hosta* 'Time Traveler' and will be referred to hereafter by its cultivar name or the "new plant". The new plant was the result of a whole plant mutation of *Hosta* 'Stitch in Time' U.S. Plant Pat. No. 18,061 discovered in a pot at a nursery in Raleigh, N.C. in the summer of 2008. 'Time Traveler' has been asexually propagated by division in the greenhouses at the same nursery in Raleigh, N.C. since 2013, and also to a limited extent by shoot tip tissue culture. The unique characteristics of the new plant have been found to be reproducible and stable in successive generations of asexually propagated plants and the resultant plants have been found to be identical to the original selection.

BRIEF SUMMARY OF THE PLANT

*Hosta* 'Time Traveler' is unique from its mutation parent and all other *Hostas* known to the inventor. The new plant differs from 'Stitch in Time' U.S. Plant Pat. No. 18,061 in that the new plant has a thin cream-white line between the chartreuse to chartreuse-yellowish margin and the gray green center variegation in the foliage. The new plant may also be compared with 'Striptease', which frequently has a similar thin line between the center and the margin variegation, but 'Striptease' is a larger plant with larger foliage and the leaves also tend to be flatter. 'Time Traveler' differs from all other *Hostas* known to the inventor in the following repeatedly observed traits in combination:

1. Broad rounded leaves with three distinct colors of variegation.
2. The wide margin emerges chartreuse and develops into a chartreuse-yellowish color.
3. The center is a narrow gray green.
4. Between the center and the margin is a thin marbled variegation of creamy-white that jets into both the margin and center and folds over the center.
5. The leaf center is crinkled as though the margin were growing faster than the center.

BRIEF DESCRIPTION OF THE DRAWINGS

The drawings of the new plant demonstrate the unique traits of 'Time Traveler' and the overall appearance of the plant at two-years-old grown in a shade garden in Raleigh, N.C. The colors are as accurate as reasonably possible with color reproductions. Variation in ambient light spectrum, source and. direction may cause the appearance of minor variation in color.

DETAILED BOTANICAL DESCRIPTION

Figure 1:
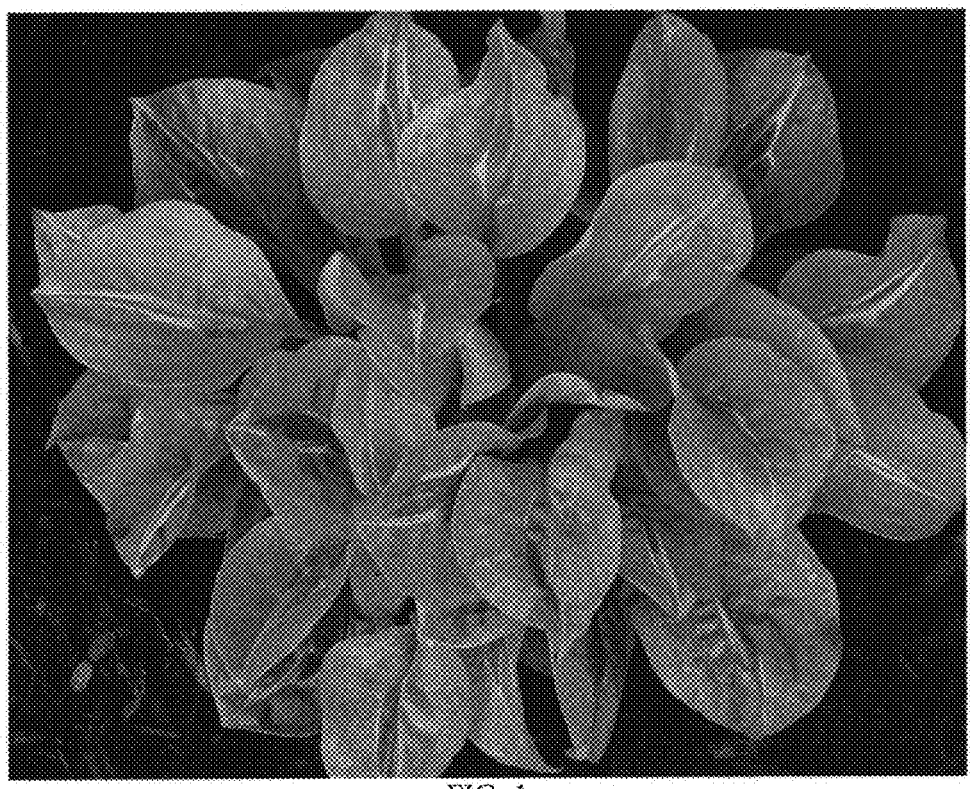
FIG. 1 shows the new plant from above with early season coloration.
Figure 2:
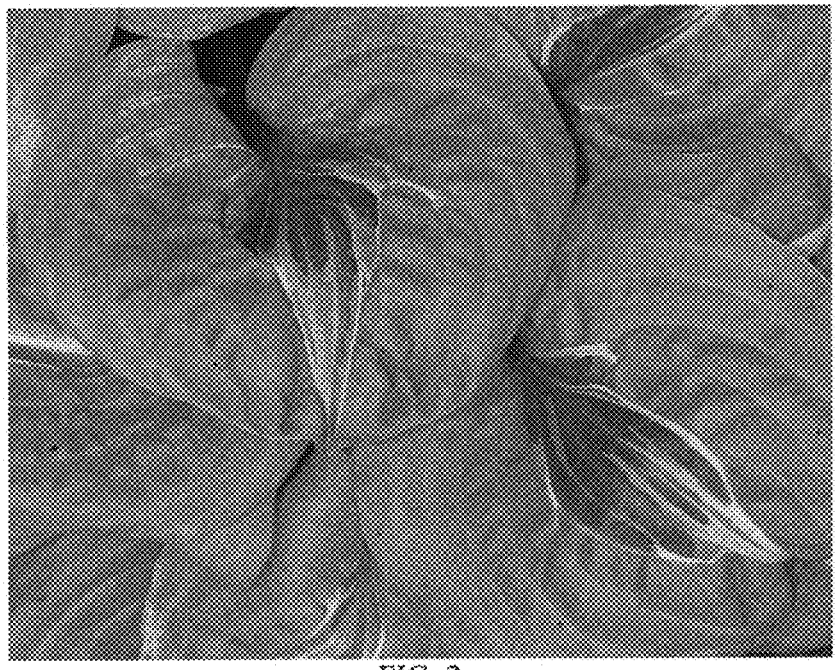
FIG. 2 shows a close-up of the variegation of the new plant.

The following descriptions and color references are based on the 2015 edition of The Royal Horticultural Society Colour Chart except where common dictionary terms are used. *Hosta* 'Time Traveler' has not been observed under all possible environments. The phenotype may vary slightly with different growing environments such as temperature, light, fertility, soil pH, moisture and maturity levels, but without any change in the genotype. The following observations and size descriptions are based on two-year-old plants in the shade trial garden of a nursery in Raleigh, N.C. and also a trial garden at a nursery in Zeeland, Mich. with supplemental fertilizer and water as needed.

Botanical classification: *Hosta* hybrid;

Parentage: Whole plant mutation of 'Stitch in Time';

Plant habit: Hardy herbaceous perennial, with acaulescent foliage; flowering and about 46 to 76 cm tall with foliage about 20 to 46 cm tall and about 38 to 107 cm wide; flowering begins mid-summer in Raleigh, N.C.;

Propagation: Division; rooting in about 14 days;

Time to produce finished crop pots: Slow to moderate; about 12 months to produce a two-quart pot from a one-inch plug;

Root: Primary roots to about 2.0 mm thick and fleshy; color creamy white to tan depending on soil type;

Leaves: Simple, acaulescent, broadly ovate; entire margin; acute apex; cordate base;

Leaf size: To about 18 to 22 cm long by about 15 to 18 cm wide;

Leaf surfaces: Glabrous and lustrous below, glabrous and slightly dull above;

Emerging leaf color: Top margin nearest RHS N144D, center nearest RHS 137A with some frosting of nearest RHS 189A and a blend of RHS 122C and RHS N138D toward the outside, creamy-white portion between margin and center nearest RHS NN155D; bottom margin nearest a blend between RHS 191C and RHS 147C, center nearest RHS N138D and creamy-white portion between margin and center nearest RHS NN155B;

Leaf color at flowering: Top margin nearest RHS 145A, center nearest RHS 137A with overlay of nearest RHS 198A, creamy-white portion between margin and center nearest RHS NN155D;

Foliage fragrance: None detected;

Veins: Campylodromous; 6 to 8 pairs, increasing to 10 to 12 pairs at maturity; pattern in center very irregular and contorted;

Vein color: Top nearest RHS 137D, bottom nearest RHS 138C;

Petiole: To about 15 cm long and 13 to 19 mm wide at base; slightly glaucous; glabrous;

Petiole color: Edge nearest RHS 144D, center nearest RHS 138C;

Inflorescence: Raceme; about 30 to 33 cm long and 8 cm wide;

Inflorescence season: About 4 weeks beginning mid-summer;

Flower bud: Spatulate; about 5.5 cm long and 10 mm wide near apex;

Flower bud color: Nearest RHS 85C;

Flowers: Perfect; funnel-shaped; typically with six tepals; about 55 mm long total with corolla tube about 15 mm long; face about 30 mm across; attitude upright to outward;

Flower longevity: About 1 day; self-cleaning;

Flower fragrance: None observed;

Tepals: Six; lanceolate; narrowly acute apex, margin entire; base fused; surface matte abaxial and adaxial; individually about 55 mm long and 10 mm wide; fused in basal 30 mm;

Tepal color: Inside nearest RHS 85D, outside nearest RHS 85D;

Pedicel: About 5 mm long and 2 mm diameter at base; slightly glaucous; curved slightly downward;

Pedicel color: Nearest RHS 138B;

Peduncle: Glaucous; cylindrical; upright in attitude; about 30 to 33 cm long and 8 mm diameter at base;

Peduncle color: Nearest RHS 138B;

Gynoecium: Single; to about 58 mm long;

*Style*.—About 55 mm long and 1 mm diameter; curved upward in last 10 mm; color nearest RHS NN155B.

*Stigma*.—3-lobed; about 2 mm across and 1 mm tall; color nearest RHS NN155C.

*Ovary*.—Three chambered; shiny; ovoid; truncate base and acute to rounded apex; about 3 mm long and 2 mm across; color nearest RHS 146D.

Androecium: Six;

*Filaments*.—Cylindrical; about 50 mm long and 1 mm diameter; color nearest RHS NN155D.

*Anther*.—Ellipsoidal; about 3 mm in length and 1 mm in width; color nearest RHS 202A.

*Pollen*.—Abundant; color nearest RHS 15B.

Floral bracts: Ovate; acute apex; truncate base; margin entire; glabrous and lustrous below, glabrous and slightly dull above typically one per flower; about 1 cm long and 3.5 cm wide;

Floral bract color: Same as leaf blades; top margin nearest RHS 145A, center nearest RHS 137A with overlay of nearest RHS 198A, creamy-white portion between margin and center nearest RHS NN155D; bottom margin nearest a blend between RHS 191C and RHS 147C, center nearest RHS N138D and creamy-white portion between margin and center nearest RHS NN155B;

Fruit and seeds have not yet been observed;

Hardiness and culture: The new plant grows best with plenty of moisture and adequate drainage; hardy to at least from USDA zone 3 though 9.

Disease and pest resistance: Not known to be more resistant to deer (*Odocoileus virginianus*) or plant-eating slugs of various genera.

I claim:

1. A new and distinct cultivar of hybrid *Hosta* plant named *Hosta* 'Time Traveler', as herein described and illustrated.

* * * * *